(12) United States Patent
Baid (10) Patent No.: US 8,784,386 B2
(45) Date of Patent: *Jul. 22, 2014

(54) NEEDLE SAFETY DEVICE

(75) Inventor: Rishi Baid, New Delhi (IN)

(73) Assignee: Poly Medicure Ltd., New Delhi (IN)

( * ) Notice: Subject to any disclaimer, the term of this patent is extended or adjusted under 35 U.S.C. 154(b) by 359 days.

This patent is subject to a terminal disclaimer.

(21) Appl. No.: 12/922,838

(22) PCT Filed: Feb. 25, 2009

(86) PCT No.: PCT/IN2009/000124
§ 371 (c)(1),
(2), (4) Date: Sep. 15, 2010

(87) PCT Pub. No.: WO2009/116080
PCT Pub. Date: Sep. 24, 2009

(65) Prior Publication Data
US 2011/0060294 A1    Mar. 10, 2011

(30) Foreign Application Priority Data
Mar. 17, 2008    (IN) .............................. 674/DEL/2008

(51) Int. Cl.
*A61M 5/32* (2006.01)
*A61M 5/00* (2006.01)
(52) U.S. Cl.
USPC ........... 604/192; 604/110; 604/197; 604/198; 604/263
(58) Field of Classification Search
USPC .......................... 604/263, 192, 197, 198, 110
See application file for complete search history.

(56) References Cited

U.S. PATENT DOCUMENTS

| 4,832,019 A | 5/1989 | Weinstein et al. |
| 4,929,241 A | 5/1990 | Kulli |
| 4,964,866 A * | 10/1990 | Szwarc ......................... 604/192 |
| 5,172,700 A | 12/1992 | Bencini et al. |
| 5,300,045 A | 4/1994 | Plassche et al. |
| 5,344,408 A | 9/1994 | Partika |
| 5,601,536 A * | 2/1997 | Crawford et al. ............. 604/263 |
| 6,616,630 B1 * | 9/2003 | Woehr et al. .................. 604/110 |

(Continued)

FOREIGN PATENT DOCUMENTS

| DE | 44 34 569 A1 | 3/1995 |
| DE | 203 15 872 U1 | 3/2004 |

(Continued)

*Primary Examiner* — Emily Schmidt
*Assistant Examiner* — Lauren M Peng
(74) *Attorney, Agent, or Firm* — Kilpatrick Townsend and Stockton LLP (57) ABSTRACT

The invention relates to a needle safety device for a medical device, the needle safety device comprising: a base portion having a bore extending in an axial direction therethrough for receiving a needle; and first and second opposing jaws extending from the base portion generally in the axial direction, wherein at least a portion of the second jaw is formed from a separate structural member connected to the base portion, wherein said portion of the second jaw is deflectable with respect to the first jaw in order to allow a needle received in the bore of the base portion to extend all the way through the needle safety device.

18 Claims, 6 Drawing Sheets

(56) References Cited

U.S. PATENT DOCUMENTS

| | | | |
|---|---|---|---|
| 6,902,546 B2* | 6/2005 | Ferguson | 604/110 |
| 7,976,502 B2* | 7/2011 | Baid | 604/164.01 |
| 8,043,265 B2* | 10/2011 | Abe et al. | 604/164.08 |
| 2002/0173752 A1 | 11/2002 | Polzin | |
| 2004/0078003 A1 | 4/2004 | Smith et al. | |
| 2005/0277879 A1* | 12/2005 | Daga | 604/110 |
| 2006/0235520 A1 | 10/2006 | Pannu | |
| 2007/0038179 A1* | 2/2007 | Bialecki et al. | 604/110 |
| 2007/0149928 A1 | 6/2007 | Kulli | |
| 2010/0222749 A1* | 9/2010 | Baid | 604/263 |
| 2011/0125096 A1* | 5/2011 | Baid | 604/164.08 |

FOREIGN PATENT DOCUMENTS

| | | |
|---|---|---|
| DE | 20 2007 009 977 U1 | 12/2007 |
| EP | 0 554 841 | 8/1993 |
| EP | 1 180 381 A1 | 2/2002 |
| EP | 1 449 554 A1 | 8/2004 |
| EP | 1 595 568 A1 | 11/2005 |
| EP | 1 752 178 A2 | 2/2007 |
| EP | 1 764 127 A2 | 3/2007 |
| WO | 97/31666 A1 | 9/1997 |
| WO | WO 99/08742 A1 | 2/1999 |
| WO | 2004/093961 A1 | 11/2004 |
| WO | 2005/042080 A1 | 5/2005 |
| WO | WO 2007061144 A1 * | 5/2007 |

* cited by examiner

NEEDLE SAFETY DEVICE

CROSS-REFERENCES TO RELATED APPLICATIONS

This application is a National Stage of International Application No. PCT/IN2009/000124 filed Feb. 25, 2009, and which claims the benefit of India Patent Application No. 674/DEL/2008, filed Mar. 17, 2008, the disclosures of which are incorporated herein by reference.

The present invention relates to a needle safety device for a medical device such as, for example, an intravenous catheter apparatus, the needle safety device comprising a base portion having a bore extending in an axial direction therethrough for receiving a needle, and first and second opposing jaws extending from the base portion generally in the axial direction.

A needle safety device of this kind is generally known and operative as a guard for the tip of a needle of the medical device by automatically covering the needle tip during withdrawal of the needle, for example, from a patient. The needle safety device thereby serves to prevent accidental pricking of, for example, a medical professional by the needle after removal of the needle from the medical device.

It is an object of the invention to provide an improved needle safety device.

This object is satisfied by a needle safety device having the features of claim 1.

The needle safety device of the invention is characterized in that at least a portion of the second jaw is formed from a separate structural member connected to the base portion, wherein said portion of the second jaw is deflectable with respect to the first jaw in order to allow a needle received in the bore of the base portion to extend all the way through the needle safety device.

According to the invention the deflectable portion of the second jaw and the first jaw are made from two separate parts. Thereby, the needle safety device can easily be adapted to needles of different thicknesses, since substantially only the diameter of the bore for receiving the needle needs to be adjusted to the thickness of the needle, whereas a reliable safety function of the needle safety device is ensured at all times due to the deflectablity of the deflectable portion of the second jaw. In addition, the needle safety device of the invention can be manufactured at low cost due to its simple design.

According to a first embodiment, the second jaw is formed from a strip of sheet metal having spring-like properties. Such a strip of sheet metal is easy and inexpensive to manufacture. Furthermore, due to its spring-like properties it may be deflected against a restoring force by a needle extending all the way through the needle safety device, such that it snaps in front of the needle tip as soon as the needle tip is moved inbetween the two jaws, thereby safely guarding the needle tip.

The strip of sheet metal may be attached to the base portion at a proximal end face thereof. In this context, the term distal designates the side of a structural member facing in the direction in which the needle tip points when the needle extends through the needle safety device, whereas the term proximal designates the opposite side.

The strip of sheet metal may have a generally L-shaped form, wherein the long leg of the L-shape extends generally in the axial direction, i.e. generally parallel to the first jaw, whereas the short leg of the L-shape extends generally perpendicularly to the axial direction. The short leg of the L-shape is used to attach the strip of sheet metal to the base portion. The strip of sheet metal may be attached to the base portion by means of a heat sealing connection.

According to a second embodiment, the second jaw comprises first and second sections that can be moved relative to each other. The first section may be formed integrally with the base portion, whereas the second section may be connected to the first section by means of a hinge. The second section hence forms the deflectable portion of the second jaw.

The first and second sections of the second jaw may be formed from two separate parts, in which case at least one pin may be formed on one of the sections and pivoted in the respective other one of the two sections.

Alternatively, the first and second sections may be formed from one piece, in which case the hinge could be a film hinge.

If the first and second sections of the second jaw are formed from two separate parts, the first section may be made from the same material as the second portion, for instance, a plastic material.

In both embodiments, the first jaw is preferably formed integrally with the base portion, since this reduces the number of parts in the needle safety device and thus adds to the simplicity thereof.

Forming the base portion, and thus preferably also the first jaw, from a plastic material helps to further reduce the costs of manufacturing the needle safety device.

If the first jaw is substantially rigid, an increased integrity of the needle safety device is achieved. At the same time, a reliable functioning of the needle safety device is ensured due to the deflectability of the second jaw.

An elastic element surrounding the first and second jaws may be provided and, in particular, arranged in the region of the deflectable portion of the second jaw. Preferably, the elastic element and the jaws are configured such that the deflectable portion of the second jaw can be spread away from the first jaw against a restoring force of the elastic element in order to allow the needle received in the bore to extend all the way through the needle safety device.

Due to the elastic element exerting its restoring force on the second jaw in the deflected state of the second jaw, which is the state in which the medical device, for example, an intravenous catheter apparatus, is typically shelved prior to use, the elastic element ensures that the spread apart jaws will snap together and guard the needle tip upon withdrawal of the needle from the medical device even after a longer shelve time, thereby continuously ensuring a correct functioning of the needle safety device. In addition, the elastic element prevents the jaws from becoming loose when the needle safety device slides along the needle, thereby further adding to a correct functioning of the needle safety device. Furthermore, the elastic element helps prevent the needle tip from protruding sideways out of the needle safety device, thereby further increasing the protecting function of the needle safety device.

The elastic element may comprise a tension ring completely surrounding the jaws, and/or a clamp, bracket, "C" clip or the like surrounding the jaws only in part.

In order to prevent the needle tip guarded by the needle safety device from protruding beyond the free ends of the jaws, the second jaw has an angled end section at its free end, which extends towards the first jaw.

Preferably, the angled end section is formed such that it is supported on the needle extending all the way through the needle safety device, thereby deflecting the second jaw, and extends across at least a portion of the free end of the first jaw, when the needle tip is located between the first and second jaws.

In order to hold the needle safety device in the medical device, for instance in an intravenous catheter apparatus, a shoulder or protrusion is formed in the region of the free end of the second jaw for engaging with a corresponding locking means formed in a housing of the medical device in which the needle safety device is to be received. Preferably, the deflection of the second jaw is such that the shoulder or protrusion of the second jaw safely engages with the locking means formed in the housing of the medical device, while the needle extends all the way through the needle safety device, whereas the shoulder or protrusion of the second jaw and the locking means of the housing are disengaged as soon as the needle tip is received between the jaws upon withdrawal of the needle and the second jaw snaps towards the first jaw due to the restoring force exerted by the second jaw and/or the elastic element.

Further subject matter of the invention is an intravenous catheter apparatus comprising: a housing defining a chamber; a needle received in the chamber; a needle safety device, in particular of the aforementioned kind, slideably arranged on the needle; and an at least part annular locking depression formed at an inner surface of the housing for receiving a locking shoulder or protrusion of the needle safety device.

By receiving the locking shoulder or protrusion of the needle safety device in the at least part annular locking depression, the needle safety device is safely held in the chamber of the housing as long as a second jaw of the needle safety device is deflected radially outwards with respect to a first jaw of the needle safety device, i.e. as long as the jaws are spread apart, as is the case when the needle extends all the way through the needle safety device.

Upon a withdrawal of the needle, for example from a patient, the jaws snap together as soon as the needle tip passes the free end of at least one of the jaws to be received between the jaws, thereby releasing the locking shoulder or protrusion of the needle safety device from the locking depression of the housing and making it possible to remove the needle safety device together with the needle from the housing of the intravenous catheter apparatus.

Apart from the fact that a locking depression is easier to manufacture than a locking protrusion, the locking depression also provides some stress relief to the second jaw in the deflected state, in particular when a needle with a larger diameter is used. The stress relief allows for an easier movement of the needle relative to the needle safety device and, specifically, relative to the second jaw. Hence, the needle can be withdrawn from the housing of the intravenous catheter apparatus with less effort.

In order to achieve a particularly safe locking of the needle safety device inside the housing, a locking protrusion may be provided which is formed adjacent the locking depression at an inner surface of the housing and extends into the chamber for engaging with the locking shoulder or protrusion of the needle safety device.

The locking depression may be a quarter- or semi-annular depression or groove, or it may extend along the complete periphery of the inner surface of the housing.

If the locking depression is part annular, for example quarter-annular or semi-annular, it is important that the needle safety device is inserted into the chamber of the housing in a correct position relative to the housing, in order to ensure that the locking shoulder or protrusion provided on a deflectable portion of the needle safety device is received in the locking depression of the housing. This can be achieved by providing a proximal end section of the chamber with a non-circular inner cross-section, for instance a part circular cross-section such as a D-shaped cross-section, which is adapted to a correspondingly non-circular outer cross-section of the needle safety device.

Since this feature of non-circular cross-sections is generally independent of the specific type of needle safety device and the specific shape of the locking depression and/or protrusion formed at the inner surface of the housing, it can be implemented in a variety of intravenous catheter apparatuses which comprise a housing defining a chamber, a needle received in the chamber and a needle safety device slideably arranged on the needle.

Preferred embodiments of the invention are described in the following description and in the accompanying drawings, wherein:

FIGS. 4a and 4b are (a) a longitudinal sectional view of the needle safety device of FIG. 1 as part of an intravenous catheter apparatus, and (b) an enlargement of a portion of FIG. 4a;

Figure 1:
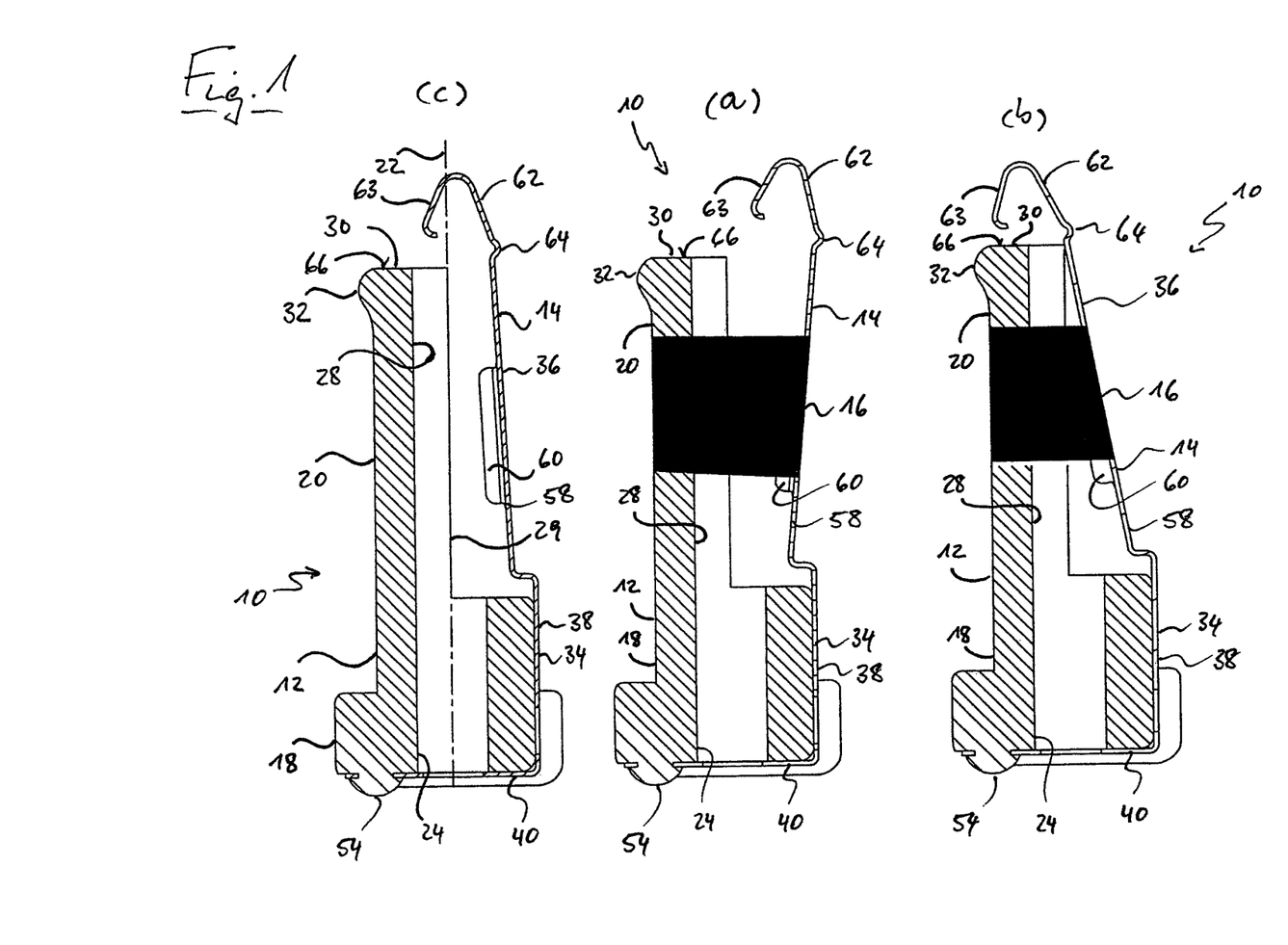
FIG. 1a to 1c are longitudinal sectional views of a first embodiment of a needle safety device of the invention (a) in a deflected state, (b) in a collapsed state, and (c) in a relaxed state without a tension ring.
Figure 2:
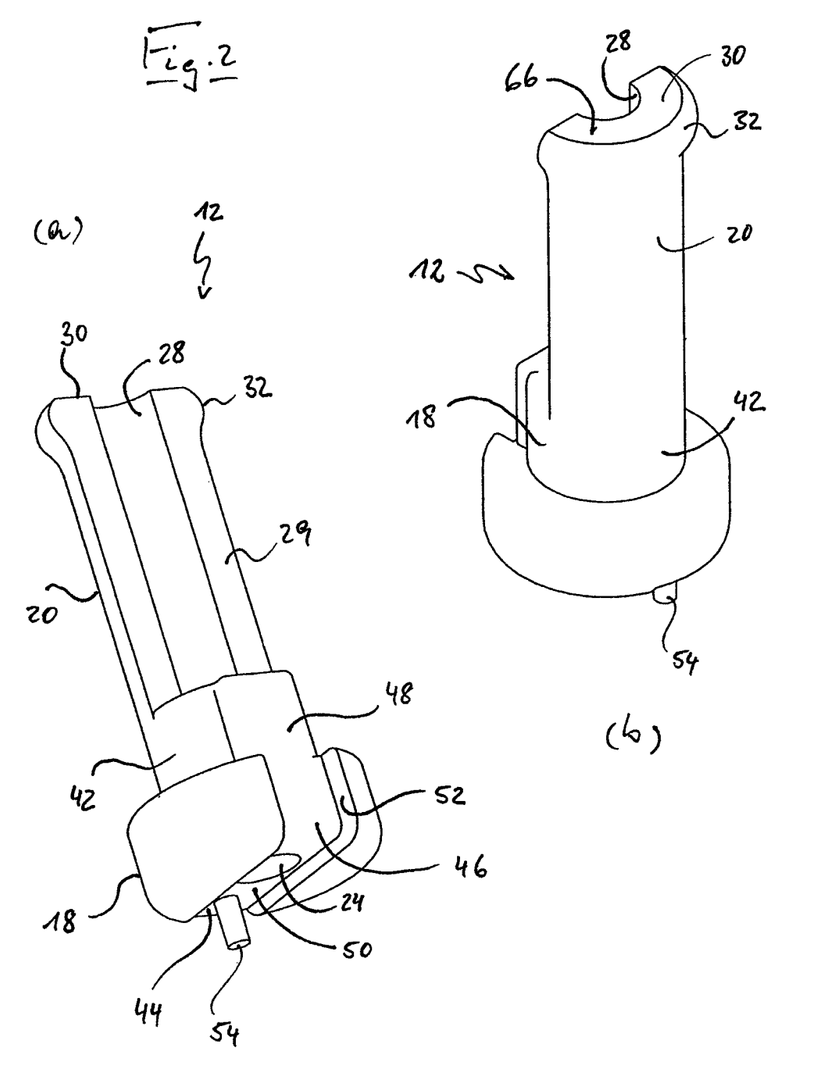
FIGS. 2a and 2b are perspective views of a main part of the needle safety device of claim 1.

FIG. 1 shows a first embodiment of a needle safety device 10 of the invention. The needle safety device 10 comprises a main part 12, a clip 14 and a tension ring 16.

Figure 4:
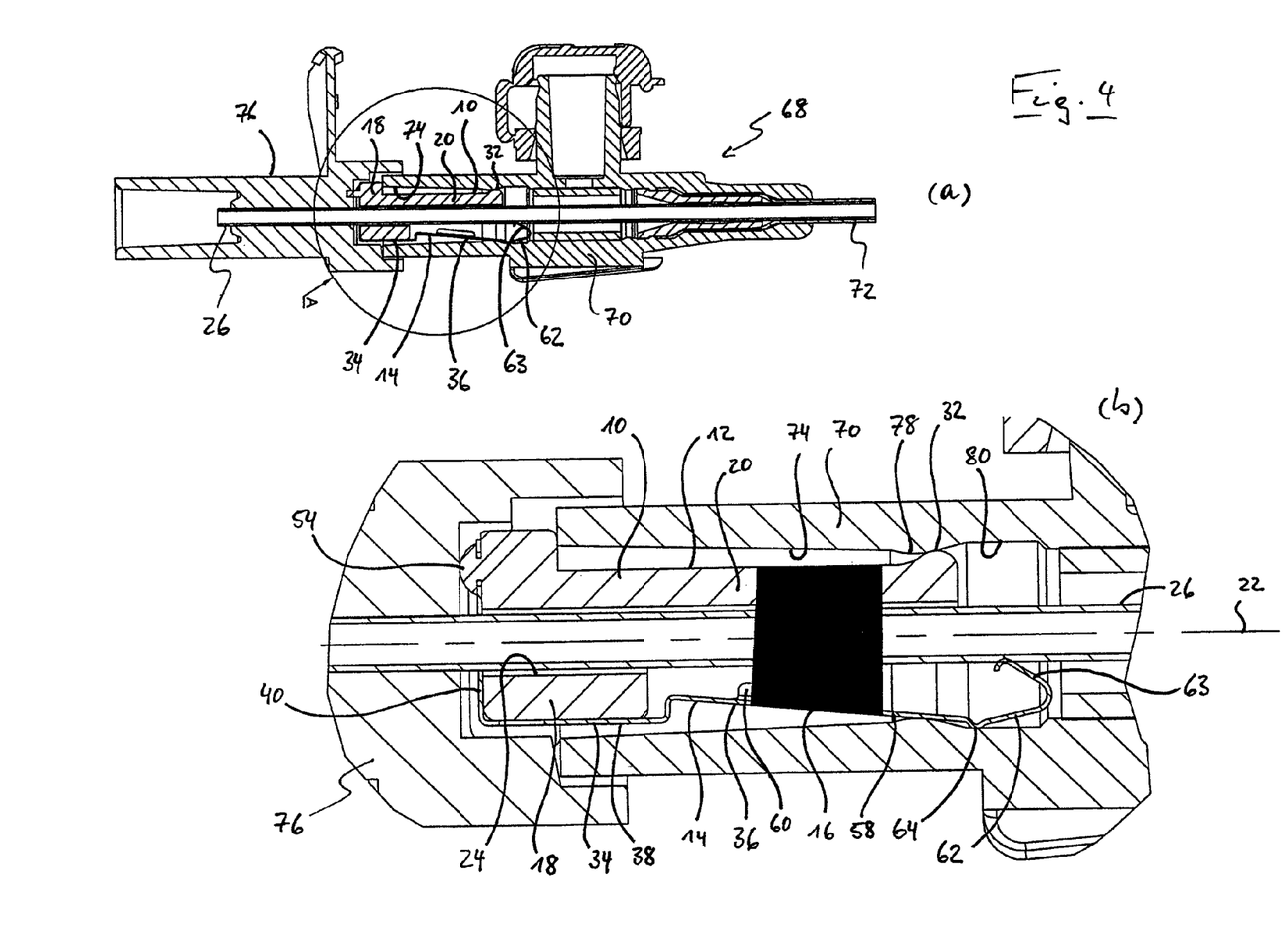

The main part 12 is made from a plastic material and comprises a base portion 18 and an elongate portion 20 forming a first jaw. The base portion 18 is of substantially cylindrical shape defining an axial direction 22, and has a bore 24 extending therethrough in the axial direction 22 for receiving a needle 26 (FIG. 4).

The elongate portion 20 is of semi-cylindrical shape and extends from the base portion 18 in the axial direction 22. The elongate portion 20 has a groove 28 formed at its flat side 29, which extends in the axial direction 22 along the entire length of the elongate portion 20 and forms an extension of the bore 24 in the base portion 18. While the bore 24 has a generally circular cross-section that is adapted to the outer profile of the needle 26, the groove 28 has a generally semi-circular cross-section.

In the region of the free or distal end 30 of the elongate portion 20, i.e. the end of the elongate portion 20 opposite from the base portion 18, the elongate portion 20 has an increased diameter resulting in a half annular protrusion 32 extending away from the flat side 29 of the elongate portion 20. The protrusion 32 operates as a locking protrusion, as will be explained in more detail in connection with FIG. 4.

Figure 3:
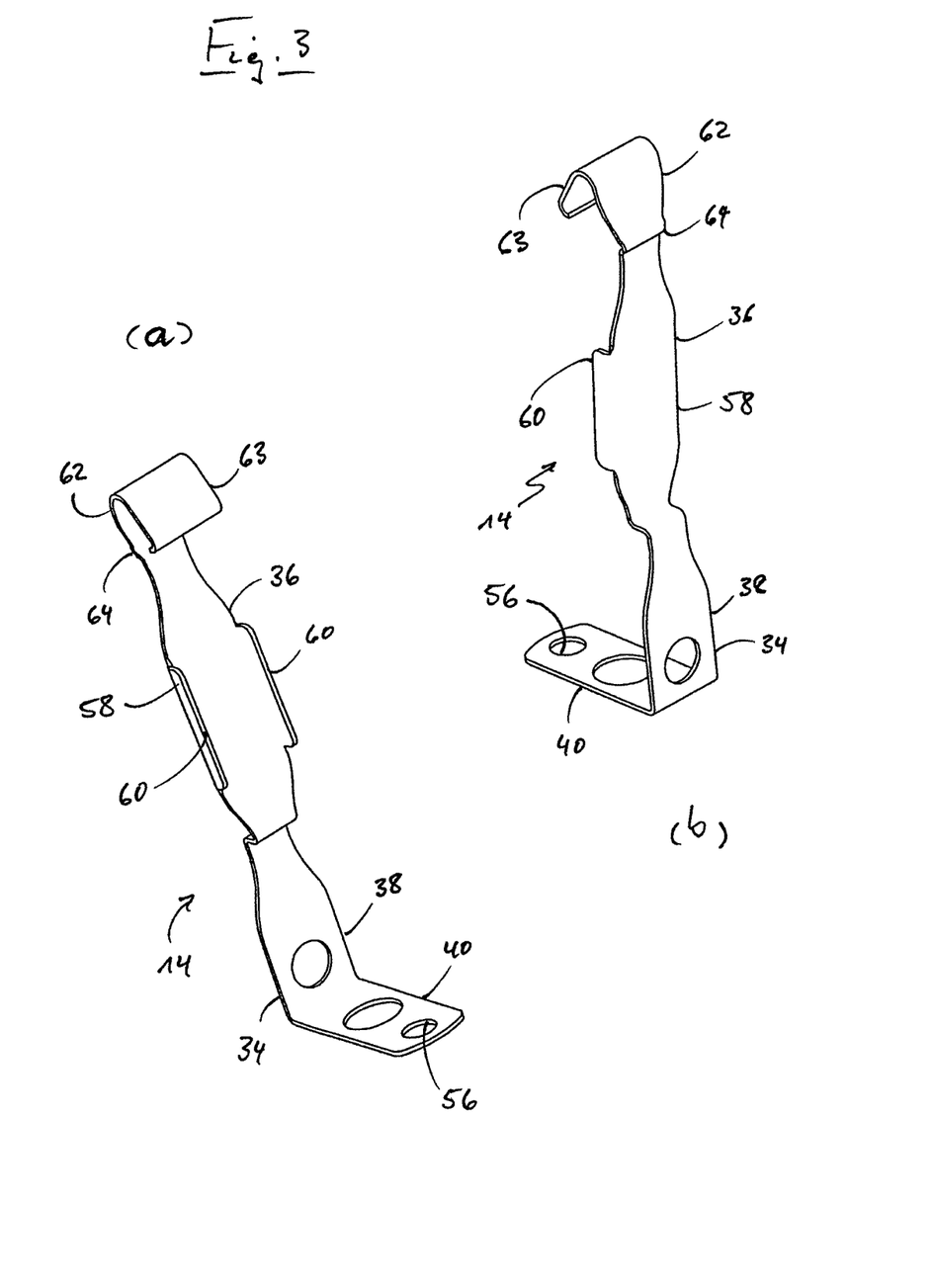
FIGS. 3a and 3b are perspective views of a steel clip of the needle safety device of FIG. 1.

The clip 14 is formed from a strip of sheet metal having spring-like properties, such as steel or the like. The clip 14 forms a second jaw and comprises a base section 34 and a deflectable section 36. The base section 34 is includes an axial section part 38 and a radial section part 40. It is adapted to engage with the base portion 18 of the main part 12 such that the axial section part 18 lies against the outer surface 42 of the base portion 18 while the radial section part 40 lies against a rear or proximal end face 44 of the base portion 18, when the clip 14 is attached to the main part 12. In order to ensure a correct positioning of the main part 12 and the clip 14, the base portion 18 is provided with a guide 46 for the clip 14, which comprises flat surface portions 48, 50 on the outer surface 42 and the end face 44, respectively, as well as sidewalls 52 defining a channel for the clip 14.

The clip 14 is secured to the main part 12 by means of a heat sealing connection. To this end, the main part 12 initially has a pillar or pin 54 formed at the proximal end face 44 and extending generally in the axial direction 22. The clip 14 has a corresponding opening 56 formed in its radial section part 40 for receiving the pillar or pin 54 when the clip 14 is mounted on the main part 12. Once the clip 14 has been brought into its correct position relative to the main part 12 the pillar or pin 54 extending through the opening 56 of the clip 14 is deformed by heat and/or pressure in order to increase the diameter of the pillar or pin 54. By making the diameter of the pillar or pin 54 larger than the diameter of the opening 56, the clip 14 is safely fixed at the main part 12.

The base section 34 of the clip 14 passes into the deflectable section 36 via a step-like bending of the sheet metal strip. The deflectable section 36 includes a straight section part 58 which is reinforced by two elongate wings 60 that extend on either side of the straight section part 58 and are bent inwards, i.e. towards the first jaw, by an angle of substantially 90°. In a relaxed state of the clip 14 mounted on the main part 12 (FIG. 1c), the straight section part 58 does not exactly extend in the axial direction 22, but is bent slightly towards the elongate portion 20 of the main part 12.

In the region of its distal end, the straight section part 58 passes into a head section part 62 which extends beyond the free end 30 of the elongate portion 20 of the main part 12. The head section part 62 has a generally V-like shape with the peak of the V pointing in the axial direction 22 and the free leg 63 of the V extending towards the elongate portion 20.

In the passage region from the straight section part 58 to the head section part 62, the sheet metal strip of the clip 14 is bent to form a protrusion 64 which extends outwardly, i.e. away from the elongate portion 20. This protrusion 64 functions as a locking protrusion as will be explained in more detail in connection with FIG. 4.

The tension ring 16 surrounds the elongate portion 20 of the main part 12 and the straight section part 58 of the clip 14 in the region of the elongate wings 60. The tension ring 16 is made from a material having elastic properties, for example rubber. The tension ring 16 is configured so that the deflectable section 36 of the clip 14 is deflected against a restoring force of the tension ring 16, when the needle 26 extends all the way through the needle safety device 10. This situation is called the deflected state of the needle safety device 10 and is shown in FIGS. 1a and 4b, wherein the needle 26 has been omitted in FIG. 1a.

When the needle 26 does not extend all the way through the needle safety device 10 or when there is no needle 26 at all, the deflectable section 36 of the clip 14 is drawn towards the elongate portion 20 of the main part 12 by the tension ring 16, as is shown in FIG. 1b. In this situation, which is referred to as the collapsed state of the needle safety device 10, the head section part 62 of the clip 14 overlaps with or extends over at least a portion of the distal end face 66 of the elongate portion 20, thereby preventing a tip of the needle 26 from protruding out of the needle safety device 10 at the distal end thereof.

FIG. 4a shows an intravenous catheter apparatus 68 and the above-described needle safety device 10 mounted therein.

The intravenous catheter apparatus 68 comprises a housing 70, for example a wing housing, having a catheter 72 extending from a distal end thereof. The housing 70 defines a chamber 74.

The needle 26 extends through the chamber 74 and through the catheter 72. In the region of its proximal end, a needle hub 76 is attached to the needle 26.

In the initial state of the intravenous catheter apparatus 68, i.e. prior to its use, the needle safety device 10 is slideably arranged on the needle 26 and inserted into the chamber 74 from the proximal end of the housing 70.

Due to the needle 26 extending all the way through the needle safety device 10, the deflectable section 36 of the clip 14 is deflected outwardly, i.e. away from the elongate portion 20 of the main part 12 and towards the inner side of the housing 70, with the head section part 62 being supported on the needle 26. Due to its deflection the deflectable section 36 and, in particular, its locking protrusion 64 abuts against the inner surface of the housing 70. At the same time, the locking protrusion 32 of the elongate portion 20 of the main part 12 is in contact with the inner surface of the housing 70.

As can be seen from FIG. 4b, an annular locking protrusion 78 extending into the chamber 74 is formed at the inner side of the housing 70. Furthermore, an annular locking depression 80 is formed adjacent the annular locking protrusion 78 on the distal side thereof.

The axial position of the annular locking protrusion 78 and the locking depression 80 is such that the locking protrusion 64 of the clip 14 is received in the locking depression 80, and both the locking protrusion 64 of the clip 14 and the locking protrusion 32 of the main part 12 engage behind the annular locking protrusion 78 of the housing 70, when the needle safety device 10 is fully inserted into the housing 70 and the needle 26 extends all the way through the needle safety device 10. Thereby the needle safety device 10 is prevented from axial movement towards the proximal end of the housing 70 as long as the needle 26 extends all the way through the needle safety device 10, even if the needle 26 is retracted from the catheter 72, for example upon withdrawal from a patient, and thereby moved relative to the needle safety device 10 (to the left in FIG. 4).

As soon as the tip of the needle 26 passes the head section part 62 of the clip 14, the deflectable section 36 is no longer supported by the needle 26. Consequently, the deflectable section 36 of the clip 14 is drawn towards the elongate portion 20 due to the restoring force of the tension ring 16, thereby bringing the needle safety device 10 into its collapsed state. In the collapsed state, the locking protrusions 32, 64 of the needle safety device 10 are disengaged from the locking depression 80 and the locking protrusion 78 of the housing 70, which allows the needle safety device 10 to be moved out of the housing 70 together with the needle 26. Once the tip of the needle 26 exits the housing 70, the needle tip is guarded by the needle safety device 10, and the needle 26 can be safely disposed of.

Figure 5:
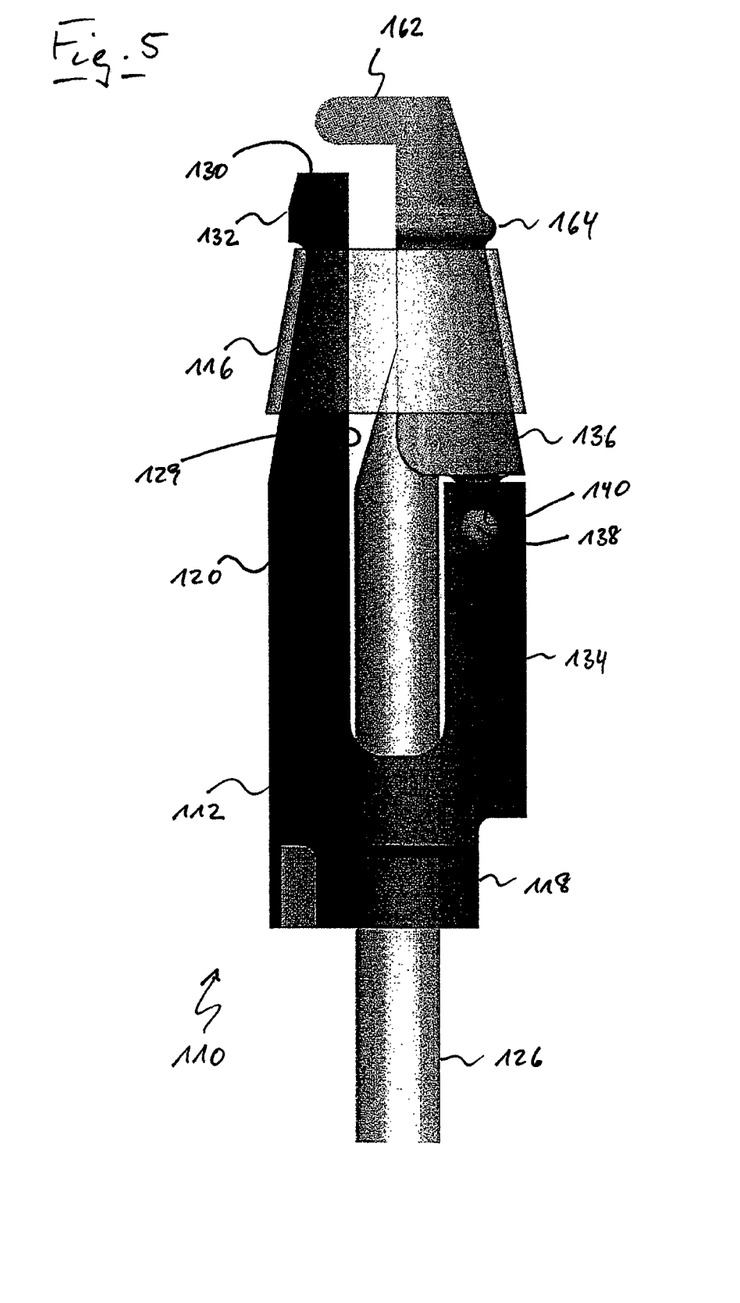
FIG. 5 is a side view of a second embodiment of a needle safety device in accordance with the invention.

Referring to FIG. 5, a second embodiment of the needle safety device 110 of the invention will now be described.

Similar to the aforementioned needle safety device 10, the needle safety device 110 shown in FIG. 5 comprises a main part 112 which may be made from a plastic material and which includes a base portion 118. The base portion 118 is of generally cylindrical shape and has a bore extending in an axial direction for receiving a needle 126.

The main part 112 further comprises a first elongate portion 120 which extends from the base portion 118 generally in the axial direction and which is also referred to as a first jaw. The first elongate portion 120 has a part circular cross-section.

The main part 112 further comprises a second elongate portion 134 extending from the base portion 118 in the axial direction and arranged opposite from the first elongate portion 120. The second elongate portion 134 also has a part-circular cross-section. The length of the second elongate portion 134 is approximately half the length of the first elongate portion 120.

The first elongate portion 120 and the second elongate portion 134 both have flat surfaces 129 facing each other and defining a space for the needle 126 to extend inbetween the elongate portions 120, 134.

The main part 112 further comprises a deflectable portion 136 which is pivotably mounted to the second elongate portion 134 in the region of the distal or free end thereof. The second elongate portion 134 and the deflectable portion 136 together form a second jaw of the needle safety device 110.

In the embodiment shown in FIG. 5, the deflectable portion 136 is mounted to the second elongate portion 134 by means of a hinge comprising two pivots 138 formed on the deflectable portion 136, which extend perpendicularly to the axial direction and which are pivoted in corresponding bores 140 provided in the second elongate portion 134.

As shown in FIG. 5, the deflectable portion 136 and the second elongate portion 134 are made from two separate parts, wherein the deflectable portion 136 preferably also comprises a plastic material. However, it will be understood that the deflectable portion 136 and the second elongate portion 134 can also be formed as an integral part, in which case the hinge connecting the deflectable portion 136 and the second elongate portion 134 could be a film hinge.

Due to the deflectable portion 136 being mounted to the second elongate portion 134 by means of a hinge, the deflectable portion 136 can be deflected outwards, i.e. away from the first elongate portion 120, about an axis perpendicular to the axial direction.

In the region of its free or distal end, the deflectable portion 136 comprises an end section 162, which extends perpendicularly to the main section of the deflectable portion 136 towards the first elongate portion 120. The length of the end section 162 is such that it passes across at least a part of the free end 130 of the first elongate portion 120, when the deflectable portion 136 is in a collapsed position, thereby making it impossible for the needle 126 to protrude out of the needle safety device 110 at the distal end thereof.

The needle safety device 110 further comprises a tension ring 116 surrounding the first elongate portion 120 and the deflectable portion 136. The tension ring 116 is made from an elastic material and configured such that the deflectable portion 136 can be deflected outwardly against a restoring force of the tension ring 116 from a collapsed position (shown in FIG. 5) to a deflected position.

In order to maintain a correct position of the tension ring 116, a section of the first elongate portion 120 opposite from the deflectable portion 136 and the deflectable portion 136 together define an outer contour of the first and second jaws, which tapers towards the distal end of the needle safety device 110 when the deflectable portion 136 is in the collapsed position.

In the region of its free end 130, a protrusion 132 is formed on the first elongate portion 120, which extends outwardly, i.e. away from the deflectable portion 136. Similarly, a protrusion 164 is formed on the deflectable portion 136, which extends outwardly, i.e. away from the first elongate portion 120. The protrusion 132 of the first elongate portion 120 and the protrusion 164 of the deflectable portion 136 are formed at approximately the same axial position.

The protrusions 132, 164 not only prevent the tension ring 116 from slipping off the jaws, but also operate as locking protrusions to lock the needle safety device 110 inside the housing 70 of, for example, an intravenous catheter apparatus 68 as has been explained in connection with FIG. 4, when the needle 126 extends all the way through the needle safety device 110 and the angled end section 162 of the deflectable portion 136 is supported on the needle 126 thereby deflecting the deflectable portion 136 outwards.

In connection with FIG. 4, the locking depression 80 of the intravenous catheter apparatus 68 provided for receiving the locking protrusions 32, 64 of the needle safety device 10 has been described to be of annular shape, i.e. to extend along the entire inner periphery of the housing 70 of the intravenous catheter apparatus 68.

However, it will be understood that the locking depression 80 need not be of complete annular shape. Instead, the locking protrusion 80 can also be of part annular shape.

Figure 6:
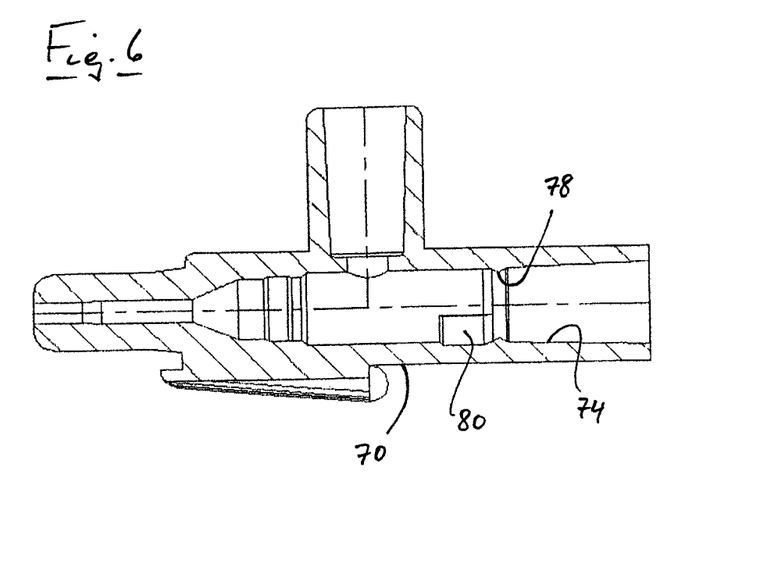
FIG. 6 is a longitudinal sectional view of an alternative embodiment of a housing of an intravenous catheter apparatus in accordance with the invention.

FIG. 6 shows an alternative embodiment of a housing 70 of an intravenous catheter apparatus 68, in which the locking depression 80 extends along less than half of the inner periphery of the housing 70, i.e. the locking depression 80 can be referred as less than semi-annular. Generally, the length of the locking depression 80 may be anything in the range from about quarter annular to full annular.

It is to be noted that in the case that the locking depression 80 is not a full annular depression but instead of part annular shape, the needle safety device 10 needs to be inserted into the housing 70 of the intravenous catheter apparatus 68 in a predefined rotational position, in order to ensure that the locking protrusion 64 of the clip 14 or of the deflectable portion 136 is safely received in the locking depression 80.

Figure 7:
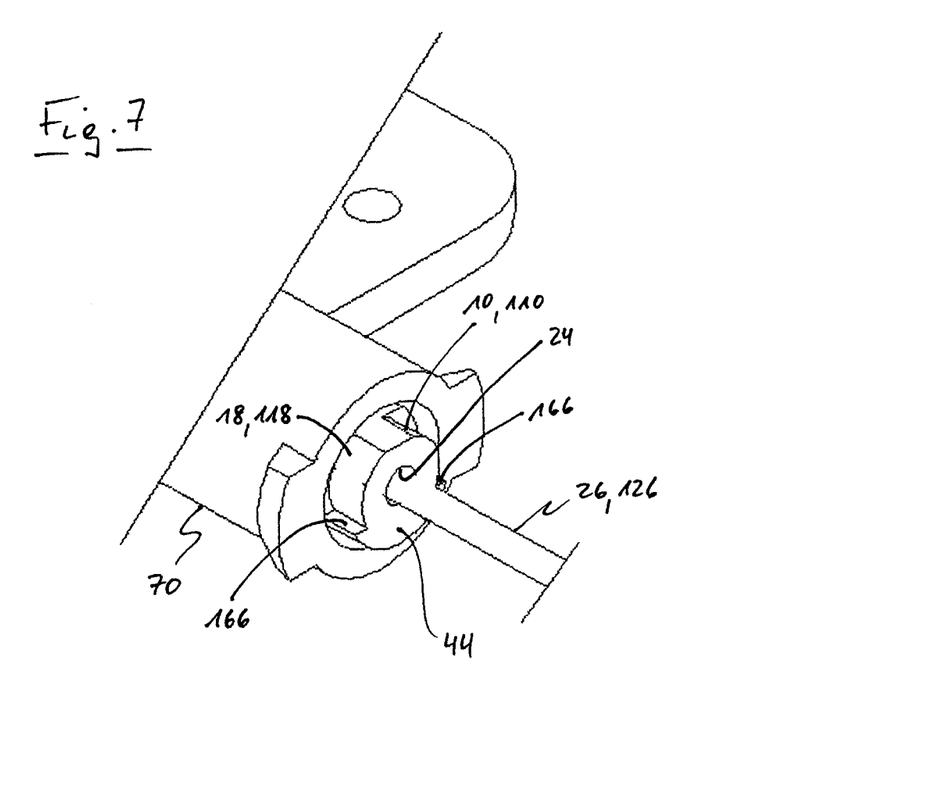
FIG. 7 is a perspective view of a proximal end portion of a housing of an intravenous catheter apparatus of the invention with a needle safety device partly inserted therein.

In order to make sure that the needle safety device 10 can be inserted into the housing 70 of the intravenous catheter apparatus 68 only in the correct rotational position, the base portion 18, 118 of the needle safety device 10, 110 may have a non-cylindrical outer profile adapted to match a correspondingly non-circular inner cross-section of the housing 70, as can be seen in FIG. 7. Specifically, the base portion 18, 118 of the needle safety device 10, 110 is provided with a part-cylindrical enlargement resulting in flat surfaces 166 formed on opposite sides of the base portion 18, 118. Opposing shoulders are formed at the inner side of the housing 70, which have corresponding flat surfaces, such that the needle safety device 10, 110 can only be inserted into the housing 70 when the flat surfaces 166 of the base portion 18, 118 are aligned with the flat surfaces of the shoulders of the housing 70.

It will be understood, that other non-cylindrical shapes of the needle safety device 10, 110 and non-circular inner cross-section of the housing 70 can be used to ensure a correct insertion of the needle safety device 10, 110 into the housing 70, as for example, oval or polygonal shapes.

REFERENCE NUMERAL LIST 10 needle safety device
12 main part
14 clip
16 tension ring
18 base portion
20 elongate portion
22 axial direction
24 bore
26 needle
28 groove
29 flat side
30 free end
32 protrusion
34 base section
36 deflectable section 38 axial section part
40 radial section part
42 outer surface
44 end face
46 guide
48 flat surface portion
50 flat surface portion
52 sidewall
54 pillar/pin
56 opening
58 straight section part
60 elongate wing
62 head section part
63 free leg
64 protrusion
66 end face
68 intravenous catheter apparatus
70 housing
72 catheter
74 chamber
76 needle hub
78 annular locking protrusion
80 locking depression
110 needle safety device
112 main part
116 tension ring
118 base portion
120 first elongate portion
126 needle
129 flat surface
130 free end
132 locking protrusion
134 second elongate portion
136 deflectable portion
138 pivot
140 bore
162 end section
164 locking protrusion
166 flat surface

I claim:

1. A needle safety device for a medical device, the needle safety device comprising:
a main body having a proximal end, the proximal end defined by a base portion having a bore extending in an axial direction therethrough for receiving a needle;
first and second opposing jaws extending from the base portion towards a tip of a received needle generally in the axial direction, the first and second opposing jaws configured to receive the needle between first jaw and second jaw;
wherein the first jaw is formed integrally with the base portion; and
wherein the second jaw comprises a distal portion and a proximal portion, the distal portion extending toward the tip of the received needle, the proximal portion having a proximal face and a distal face and extending transverse to the axial direction;
wherein at least a portion of the second jaw is formed from a strip of sheet metal having spring-like properties, wherein the distal face of the proximal portion of the second jaw attaches to the main body by overlapping with a proximal end face of the base portion, wherein the distal portion of the second jaw is deflectable with respect to the first jaw in order to allow the needle received in the bore of the base portion to extend all the way through the needle safety device.

2. The needle safety device of claim 1, wherein the strip of sheet metal is attached to the base portion by means of a heat sealing connection.

3. The needle safety device of claim 1, wherein the second jaw comprises first and second sections that can be moved relative to each other.

4. The needle safety device of claim 3, wherein the first section is formed integrally with the base portion.

5. The needle safety device of claim 3, wherein the second section is connected to the first section by means of a hinge.

6. The needle safety device of claim 3, wherein the second section is made from a same material as the first section.

7. The needle safety device of claim 1, wherein the first jaw is rigid.

8. The needle safety device of claim 1, wherein the base portion is formed from a plastic material.

9. The needle safety device of claim 1, further comprising an elastic element at least partly surrounding the first and second jaws.

10. The needle safety device of claim 9, wherein the elastic element is arranged in a region of the deflectable portion of the second jaw.

11. The needle safety device of claim 1, wherein the second jaw has an angled end section at the second jaw's free end, which extends towards the first jaw.

12. The needle safety device of claim 11, wherein the angled end section is formed such that the section is supported on the needle extending all the way through the needle safety device thereby deflecting the second jaw, and extends across at least a portion of a free end of the first jaw when the tip of the needle is located between the first and second jaws.

13. The needle safety device of claim 1, wherein a shoulder or protrusion is formed in the region of a free end of the second jaw for engaging behind a corresponding locking protrusion formed in a housing of the medical device, in which the needle safety device is to be received.

14. An intravenous catheter apparatus comprising:
a housing defining a chamber;
a needle received in the chamber;
a needle safety device slidably arranged on the needle, the needle safety device comprising:
a main body having a proximal end, the proximal end defined by a base portion having a bore extending in an axial direction therethrough for receiving the needle; and
first and second opposing jaws extending from the base portion toward a tip of the received needle generally in the axial direction, the first and second opposing jaws configured to receive the needle between first jaw and second jaw;
wherein the first jaw is formed integrally with the base portion;
wherein the second jaw comprises a distal portion and a proximal portion, the distal portion extending toward the tip of the received needle, the proximal portion having a proximal face and a distal face and extending transverse to the axial direction;
wherein at least a portion of the second jaw is formed from a strip of sheet metal having spring-like properties, wherein the distal face of the proximal portion of the second jaw attaches to the main body by overlapping with a proximal end face of the base portion, wherein the distal portion of the second jaw is deflectable with respect to the first jaw in order to allow the needle received in the bore of the base portion to extend all the way through the needle safety device; and an at least part annular locking depression formed at an inner surface of the housing for receiving a locking shoulder or protrusion of the needle safety device.

15. The intravenous catheter apparatus of claim 14, further comprising a locking protrusion formed adjacent the locking depression at the inner surface of the housing and extending into the chamber for engaging with the locking shoulder or protrusion of the needle safety device.

16. The intravenous catheter apparatus of claim 14, wherein a proximal end section of the chamber has a non-circular inner cross-section adapted to a correspondingly non-circular outer cross-section of the needle safety device.

17. An intravenous catheter apparatus comprising:
a housing defining a chamber;
a needle received in the chamber; and
a needle safety device slidably arranged on the needle, the needle safety device comprising:
a main body having a proximal end, the proximal end defined by a base portion having a bore extending in an axial direction therethrough for receiving the needle; and
first and second opposing jaws extending from the base portion toward a tip of the received needle generally in the axial direction, the first and second opposing jaws configured to receive the needle between first jaw and second jaw;
wherein the first jaw is formed integrally with the base portion;
wherein the second jaw comprises a distal portion and a proximal portion, the distal portion extending toward the tip of the received needle, the proximal portion having a proximal face and a distal face and extending transverse to the axial direction;
wherein at least a portion of the second jaw is formed from a strip of sheet metal having spring-like properties, wherein the distal face of the proximal portion of the second jaw attaches to the main body by overlapping with a proximal end face of the base portion, wherein the distal portion of the second jaw is deflectable with respect to the first jaw in order to allow the needle received in the bore of the base portion to extend all the way through the needle safety device; and wherein
a proximal end section of the chamber has a non-circular inner cross-section adapted to a correspondingly non-circular outer cross-section of the needle safety device.

18. A needle safety device for a medical device, the needle safety device comprising:
a main body having a proximal end, the proximal end defined by a base portion formed from a plastic material and having a bore extending in an axial direction therethrough for receiving a needle;
first and second opposing jaws extending from the base portion towards a tip of a received needle generally in the axial direction, the first and second opposing jaws configured to receive the needle between first jaw and second jaw;
wherein the first jaw is formed integrally with the base portion; and
wherein at least a portion of the second jaw is formed from a strip of sheet metal having spring-like properties, the portion of the second jaw attached to a proximal end face of the base portion, wherein said portion of the second jaw is deflectable with respect to the first jaw in order to allow the needle received in the bore of the base portion to extend all the way through the needle safety device.

* * * * *